United States Patent [19]

Gould et al.

[11] Patent Number: 4,628,134
[45] Date of Patent: Dec. 9, 1986

[54] MULTISTAGE PROCESS FOR CONVERTING OXYGENATES TO ALKYLATED LIQUID HYDROCARBONS

[75] Inventors: Ronald M. Gould, Sewell; Samuel A. Tabak, Wenonah, both of N.J.

[73] Assignee: Mobil Oil Corporation, New York, N.Y.

[21] Appl. No.: 779,347

[22] Filed: Sep. 23, 1985

Related U.S. Application Data

[63] Continuation-in-part of Ser. No. 692,261, Jan. 17, 1985, Pat. No. 4,543,435, and a continuation-in-part of Ser. No. 733,994, May 14, 1985, Pat. No. 4,579,999.

[51] Int. Cl.$^4$ .......................... C07C 1/20; C07C 2/00
[52] U.S. Cl. .................................... 585/331; 585/315; 585/316; 585/640; 585/709; 585/723
[58] Field of Search ............... 585/709, 331, 315, 316, 585/640, 723

[56] References Cited

U.S. PATENT DOCUMENTS

| | | | |
|---|---|---|---|
| 3,172,834 | 3/1965 | Kozlowski | 585/331 |
| 3,972,958 | 8/1976 | Garwood et al. | 585/469 |
| 3,985,823 | 10/1976 | Sobel et al. | 585/331 |
| 4,048,250 | 9/1977 | Garwood et al. | 585/469 |
| 4,211,885 | 7/1980 | Banks | 585/415 |
| 4,260,841 | 4/1981 | Holland et al. | 585/640 |
| 4,262,155 | 4/1981 | Hutson, Jr. | 585/331 |
| 4,387,263 | 6/1983 | Vogt et al. | 585/640 |
| 4,423,274 | 12/1983 | Daviduk et al. | 585/640 |
| 4,542,252 | 9/1985 | Graziani et al. | 585/640 |
| 4,543,435 | 9/1985 | Gould et al. | 585/330 |

*Primary Examiner*—Asok Pal
*Attorney, Agent, or Firm*—A. J. McKillop; M. G. Gilman; L. G. Wise

[57] ABSTRACT

Alkylate is produced by catalytically converting oxygenate feedstock, such as methanol, to lower olefins comprising $C_2$–$C_4$ olefins. Ethene is separated for recycle and an isoparaffin is alkylated with $C_3$–$C_4$ olefins.

19 Claims, 3 Drawing Figures

MULTISTAGE PROCESS FOR CONVERTING OXYGENATES TO ALKYLATED LIQUID HYDROCARBONS

REFERENCE TO COPENDING APPLICATION

This application is a continuation-in-part of U.S. patent applications Ser. No. 692,261 filed 17 Jan. 1985 now U.S. Pat. No. 4,543,435, and Ser. No. 733,994 filed 14 May 1985 now U.S. Pat. No. 4,579,999, incorporated herein by reference.

BACKGROUND OF THE INVENTION

This invention relates to an integrated system for converting oxygenates, such as methanol or dimethyl ether (DME), to liquid hydrocarbons. In particular it provides a continuous process for producing $C_7+$ hydrocarbon products by converting the oxygenate feedstock catalytically to an intermediate lower olefinic stream and alkylating isobutane with olefins to produce distillate and/or gasoline.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making diesel fuel by a multi-stage technique.

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of new industrial processes.

The medium pore ZSM-5 type catalysts are useful for converting methanol and other lower aliphatic alcohols or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), 4,423,274 (Daviduk et al) and 4,433,189 (Young), incorporated herein by reference. It is generally known that the MTO process can be optimized to produce a major fraction of $C_2$-$C_4$ olefins. Prior process proposals have included a separation section to recover ethene and other gases from byproduct water and $C_5+$ hydrocarbon liquids.

SUMMARY OF THE INVENTION

It has been discovered that methanol, DME or the like may be converted to liquid fuels, particularly alkylate, in a multi-stage continuous process, with integration between the major process units providing an ethene-rich recycle stream. The initial stage MTO type process hydrocarbon effluent stream, after byproduct water separation, can be fed to an alkylation stage for conversion to heavier hydrocarbons. Ethene may be recovered by interstage separation and recycled. Advantageously, the recycled ethene is found to be reactive with methanol/DME or other oxygenates in the presence of ZSM-5 type catalysts. In effect a novel MTO-Alkylation system is provided wherein the ethene component may be recycled sustantially to extinction.

In a preferred embodiment, the invention provides methods and apparatus for an integrated continuous technique for converting Oxygenated organic feedstock to liquid alkylate hydrocarbons comprising means for (a) contacting feedstock with zeolite catalyst in a primary catalyst stage at elevated temperature and moderate pressure to convert at least a portion of the feedstock oxygenate to hydrocarbons containing a major fraction of $C_2$-$C_4$ olefins and a minor fraction containing $C_5+$ hydrocarbons;

(b) cooling and separating effluent from step (a) to provide an aqueous liquid byproduct stream, a heavy hydrocarbon liquid stream and a light hydrocarbon vapor stream rich in $C_2$-$C_4$ olefins;

(c) compressing at least a portion of the olefinic light hydrocarbon stream to condense a liquid olefinic hydrocarbon stream rich in $C_3+$ olefins and recovering an ethene-rich gaseous stream;

(d) further contacting substantially all of the condensed liquid olefinic hydrocarbon stream with a tertiary alkane stream in a secondary catalytic stage with acid alkylation catalyst at increased pressure to convert at least a portion of olefins to a heavier liquid alkylate hydrocarbon product stream comprising $C_7+$ gasoline and distillate range liquids; and (e) recovering ethene in a gaseous stream for recycle to the primary catalytic stage.

Advantageously, the primary stage catalyst comprises ZSM-5 type zeolite and ethene is recycled to the primary stage at a rate of about 1 to 20 parts ethene per 100 parts by weight of methanol equivalent in the feedstock. By fractionating gaseous effluent separated from the primary staged effluent, a recycle gas stream may be recovered containing at least 90% of ethene from the primary catalytic stage. An olefinic stream rich in $C_3+$ olefins, especially propene and butylenes, is provided for reaction with various isoparaffins, such as isobutane.

Other objects and features of the invention will be seen in the following description and drawings.

The Drawings

DESCRIPTION OF PREFERRED EMBODIMENTS

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH + CH_3OCH_3 + H_2O$) is produced by partial dehydration. This reaction takes place in either conversion of methanol to lower olefins (MTO) or methanol to gasoline (MTG).

The zeolite catalysts preferred for use herein include the crystalline aluminosilicate zeolites having a silica to alumina ratio of at least 12, a constraint index of about 1 to 12 and acid cracking activity of about 1–200. Representative of the ZSM-5 type zeolites are ZSM-5, ZSM-11, ZSM-12, ZSM-22, ZSM-23, ZSM-35, ZSM-48 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxygenate conversion is HZSM-5 zeolite with alumina binder. These medium pore shape selective catalysts are sometimes known as porotectosilicates or "pentasil" catalysts.

Other catalysts and processes suitable for converting methanol/DME to lower olefins are disclosed in U.S. Pat. No. 4,393,265 (Bonifaz), U.S. 4,387,263 (Vogt et al.) and European Pat. Application No. 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated. Various reactor configurations may be used including fluidized bed catalytic reactors, moving bed and fixed bed reactors.

Figure 1:
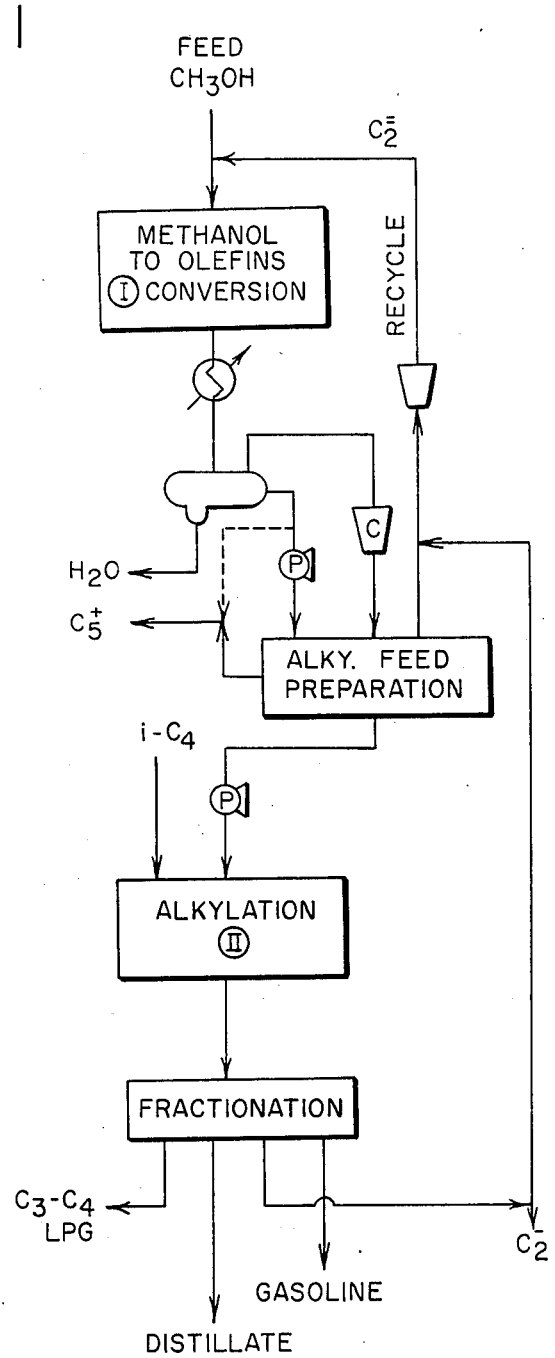
FIG. 1 is a process flow sheet showing the major unit operations and process streams.

Referring to FIG. 1, the process feedstock (methanol or DME, for instance) is fed to the primary stage (I) where it is converted to lower olefins and gasoline hydrocarbon plus water by dehydration of the oxygenated feedstock. Byproduct water is recovered by simple phase separation from the cooled effluent. Liquid hydrocarbons consisting essentially of $C_5+$ gasoline range materials may be recovered or pumped to the higher secondary stage pressure. At least a portion of the vapor phase effluent from the primary stage is compressed to alkylation reaction pressure, and reacted at high pressure and moderate temperature in contact with acidic alkylation catalyst. Secondary stage (II) effluent is then separated into light gases for recycle in part, $C_7+$ gasoline and/or distillate range hydrocarbons.

Alkylation of ethylene with methanol over ZSM-5 catalyst has been described by Kaeding et al (*J. Catalysis*; Jan. 1980, Aug. 1984), and it is known to recycle ethene in the production of aromatic gasoline from methanol over zeolites (U.S. Pat. No. 3,998,899, Daviduk). In a fluidized bed plant for converting methanol to lower olefins and gasoline, recycle of ethylene at a rate of 2.5 parts by weight be 100 parts $CH_2$ equivalent in the feedstock methanol provides a product yield that is substantially the same, as shown in Table I. These continuous runs are conducted at the same conditions.

TABLE I

| | Hydrocarbon Product Yield, Wt % | |
|---|---|---|
| Component | Without Recycle | With ethene Recycle |
| $C_1$ | 0.8 | 0.8 |
| $C_2$ | 0.3 | 0.3 |
| $C_2=$ | 2.5 | 2.7 |

TABLE I-continued

| | Hydrocarbon Product Yield, Wt % | |
|---|---|---|
| Component | Without Recycle | With ethene Recycle |
| $C_3$ | 4.4 | 4.5 |
| $C_3=$ | 4.6 | 4.5 |
| $nC_4$ | 2.1 | 2.1 |
| $iC_4$ | 10.8 | 10.4 |
| $C_4=$ | 5.4 | 5.1 |
| $C_5+$ (Gasoline) | 69.1 | 69.6 |
| Total | 100.0 | 100.0 |

T = 407° C.
P = 400 KPa,
WHSV = 2.65⁻ hr (based on HZSM-5 catalyst).

The process may be optimized by employing fluid bed primary stage conditions in the temperature range of about 425° to 550° C., a pressure range of about 100 to 800 kPa and weight hourly space velocity range of about 0.5 to 3.0 based on ZSM-5 equivalent catalyst and methanol equivalent in the primary stage feedstock. Suitable fluid bed equipment and operating conditions are described in U.S. Pat. application Ser. No. 687,045, filed 28 Dec. 1984, incorporated herein by reference. Fixed bed MTO systems are described in U.S. Pat. No. 4,542,252 (Graziani et al).

Figure 2:
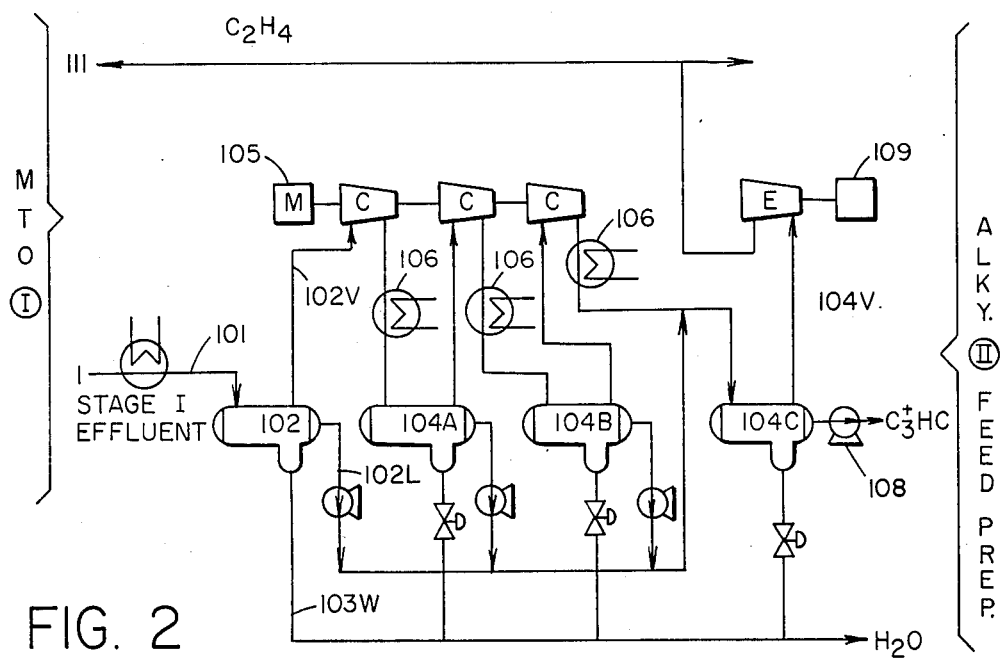
FIG. 2 is a schematic representation of a preferred inter-stage separation system for ethene recovery.

In the embodiment of Fig. 2, the light hydrocarbon vapor stream separated from the primary stage effluent is compressed in a plurality of compression stages to condense liquid olefinic hydrocarbons. The full reaction effluent of the primary stage MTO plant is passed via conduit 101 and primary phase separator 102 to provide a first vapor stream 102V, rich in $C_4$-hydrocarbons, liquid hydrocarbons stream 102L, and by product water stream 103W. The liquid (eq-$C_5+$) stream 102L is combined with a corresponding liquid HC from succeeding separators and withdrawn. The primary vapor stream 102V is adiabatically compressed by multi-stage motor-compressor set 105, cooled via exchanger 106 and passed to a succeeding separator 104A, at which point the preceeding phase separation technique is repeated. Likewise other separators 104B and 104C operate to provide an ethene-rich recycle stream 104V, which is passed to turbo-expander 109E and thus at MTO pressure back via line 111 to the olefins production in the primary staqe. Advantageously, the MTO effluent is received at about atmospheric pressure (eg, 100–150 kPa) and compressed in plural stages to a pressure of about 1100–3500 kPa (150–400 psig) and separated in the final vessel 104C at about ambient temperature (20°–60° C.). Olefinic liquids rich in $C_3+$ aliphatic are recovered from the final compressor stage via pump 108 which passes the liquid HC stream to the following secondary stage alkylation unit.

Figure 3:
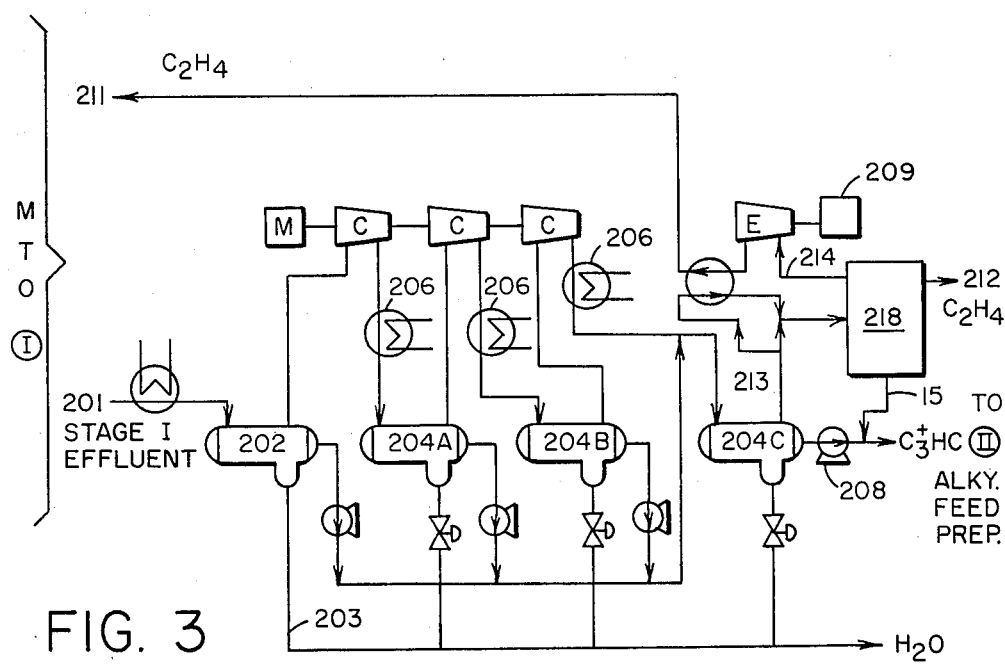
FIG. 3 is a schematic representation of an alternative system.

A further modification of the interstage ethene separation technique described above is depicted in the flow diagram in Fig. 3, wherein corresponding apparatus and process streams are identified by corresponding numbers. In this adaption, ethene-rich vapor withdrawn from the last separator 204C via line 213 is cooled by heat exchanged and further processed to increase ethene purity in ethylene unit 218. As will be understood by one skilled in the art, ethene can be treated in a cryogenic plant cold box, de-ethanizer tower, absorption unit or the like to remove undesirable components prior to recycle 211 and/or recovery 212. A suitable selective sorption unit is disclosed in U.S. Pat. No. 4,471,147 (Hsia et al), incorporated herein by reference.

Preferably, compressed light hydrocarbons are fractionated to recover a recycle stream containing at least 90 mole percent ethene. This can be achieved by selectively absorbing $C_3^+$ components in a $C_5^+$ liquid hydrocarbon sorbent stream.

The secondary stage alkylation process employed herein is a well known industrial technique for reacting alkenes with tertiary alkanes (isoparaffins), such as isobutane, isopentane, isohexane, etc. The resulting product is a $C_7^+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21-41 MPa (3000-6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular hydrocarbons involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylation of isobutane with propene are mainly 2,3- and 2,4-dimethylpentane. Propene is alkylated preferrably as a component of a $C_3$-$C_4$ fraction. HF catalysts for alkylation of isobutane with 1- and 2-butenes give both dimethylhexanes and trimethylpentanes. The product obtained from alkylation of isobutane with isobutylene at low temperature (e.g., $-25°$ C.) with hydrogen fluoride is 2,2,4-trimethylpentane.

During use the acid catalysts may become diluted with byproduct hydrocarbons and as a result decrease in activity. Sulfuric acid concentrations are maintained at about 90%. Hydrogen fluoride concentrations of 80-90% are common, although the optimum concentration depends on the reaction temperature and reactor geometry. Operation below these acid concentrations generally causes incomplete conversion or polymerization. With sulfuric acid, the product quality is improved when temperatures are reduced to the range of 0°-10° C. Cooling requirements are obtained by low temperature flashing of unreacted isobutane. With hydrogen fluoride, the process is less sensitive to temperature, and temperatures of 0°-40° C. can be used. Some form of heat removal is essential because the heat of reaction is approximately $14 \times 10^5$ J/kg (600 Btu/lb) of butenes. Typically the elevated pressure for alkylation by these acid catalysts is about 1500 to 3000 kPa (200-300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive i-$C_4H_8$ readily alkylates to give an excellent product. The alkylation of pure 1-$C_4H_8$ by itself oroceeds with considerable isomerization of the 1-$C_4H_8$ to 2-$C_4H_8$ followed by alkylation to give a highly branched product. The presence of i-$C_4H_8$ accelerates the alkylation reaction and allows less time for olefin isomerization. Consequently the reaction produces an alkylate with a lowered antiknock value. For the sulfuric acid system, i-$C_4H_8$ tends to oligomerize and causes other side reaction products of inferior quality; but the isomerization of 1-$C_4H_8$ to 2-$C_4H_8$ proceeds more completely, thereby favoring formation of superior products. Thus for mixed olefin feeds such as described above, the two factors with both catalyst systems counteract each other to provide products of similar antiknock properties.

The olefin-producing MTO process may simultaneously generate isobutane, but the amount may be insufficient to alkylate the coproduced olefins. A suitable outside source of isobutane is natural gas or a byproduct of methanol-to-gasoline (MTG) processes.

Suitable alkylation processes are described in U.S. Pat. Nos. 3,879,489 (Yurchak et al), 4,115,471 (Kesler). 4,377,721 (Chester) and in the Kirk-Othmer Encyclopedia of Chemical Technology, Vol. 2, pp. 50-58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

We claim:
1. An integrated continuous process for converting oxygenated organic feedstock to liquid hydrocarbons comprising the steps of
 (a) contacting feedstock with zeolite catalyst in a primary catalyst stage at elevated temperature and moderate pressure to convert at least a portion of the feedstock oxygenate to hydrocarbons containing a major fraction of $C_2$-$C_4$ olefins and a minor fraction containing $C_5^+$ hydrocarbons;
 (b) cooling and separating effluent from step (a) to provide an aqueous liquid byproduct stream, a heavy hydrocarbon liquid stream and a light hydrocarbon vapor stream rich in $C_2$-$C_4$ olefins;
 (c) compressing at least a portion of the olefinic light hydrocarbon stream to condense a liquid olefinic hydrocarbon stream rich in $C_3$-$C_4$ olefins and recovering an ethene-rich gaseous stream;

(d) further reacting the condensed liquid olefinic hydrocarbon stream from step (c) with isobutane in a secondary alkylation stage with acid catalyst to convert at least a portion of $C_3$-$C_4$ olefins to a heavier $C_7+$ liquid hydrocarbon product stream comprising alkylate gasoline; and (e) recycling ethene in a gaseous stream to the primary catalytic stage.

2. The process of claim 1 further comprising the of fractionating gaseous effluent from separation step (b) to recover a recycle gas stream containing at least 90% of ethene from the primary catalytic stage and an olefinic stream rich in $C_3+$ olefins.

3. The process of claim 1 wherein the primary stage catalyst comprises ZSM-5 type zeolite and ethene is recycled to the primary stage at a rate of about 1 to 20 parts ethene per 100 parts by weight of methanol equivalent in the feedstock.

4. The process of claim 1 wherein primary stage feedstock comprising methanol and/or dimethyl ether and recycled ethene are converted over HZSM-5 catalyst to provide a light olefinic hydrocarbon vapor stream comprising a major amount of $C_3$-$C_4$ olefins and a minor amount of ethene.

5. The process of claim 4 wherein olefin production is optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock.

6. The process of claim 5 wherein at least 90% of feedstock is converted per reactor pass and wherein water diluent is cofed with methanol and/or dimethyl ether in a molar ratio of about 0.01:1 to 2:1.

7. The process of claim 4 wherein primary stage hydrocarbon effluent contains about 1 to 10 wt.% ethene and about 10 to 60 wt. % $C_3$-$C_4$ olefins.

8. The process of claim 4 wherein ethene is recovered from the primary stage effluent vapor stream by fractionation.

9. The process of claim 1 wherein the secondary stage effluent is cooled and separated to provide a light hydrocarbon stream containing unconverted ethene and wherein said unconverted ethene is expanded to about primary stage pressure for recycle.

10. The process of claim 9 wherein compressed light hydrocarbon vapor is recompressed to recover an ethene-rich recycle Stream.

11. The process of claim 1 wherein the secondary alkylation stage comprises a liquid phase reaction catalyzed by HF.

12. A process for converting oxygenate feedstock comprising methanol, dimethyl ether or mixtures thereof to liquid hydrocarbons comprising the steps of contacting the feedstock with zeolite catalyst in a primary catalyst stage at elevated temperature and moderate pressure to convert feedstock to hydrocarbons comprising $C_2$-$C_4$ olefins and $C_5+$ hydrocarbons;

cooling and separating effluent from the primary stage to recover a liquid hydrocarbon stream and a light hydrocarbon vapor stream rich in $C_2$-$C_4$ olefins;

compressing the olefinic light hydrocarbon stream to condense a liquid olefinic hydrocarbon stream rich in $C_3+$ olefins and recovering an ethene-rich gaseous stream;

further reacting the condensed liquid olefinic hydrocarbon stream with a tertiary alkane in a secondary catalytic stage with acid alkylation catalyst at substantially increased pressure under liquid conditions to convert at least a portion of olefins to a heavier liquid hydrocarbon product stream comprising alkylate gasoline and/or distillate range liquids; and recycling ethene in a gaseous stream to the primary catalytic stage.

13. The process of claim 12 wherein primary stage feedstock is converted over HZSM-5 catalyst to provide a light olefinic hydrocarbon vapor stream comprising a major amount of $C_3$-$C_4$ olefins and a minor amount of ethene.

14. The process of claim 12 further comprising the step of fractionating gaseous effluent separated from primary stage effluent to recover a recycle gas stream containing at least 90% of ethene from the primary catalytic stage and an olefinic stream rich in $C_3+$ olefins.

15. The process of claim 12 wherein the primary stage catalyst comprises ZSM-5 type zeolite and ethene is recycled to the primary stage at a rate of about 1 to 10 parts ethene per 100 parts by weight of methanol equivalent in the feedstock.

16. The process of claim 12 wherein the light hydrocarbon vapor stream separated from the primary stage effluent is compressed in a plurality of compression stages to condense liquid olefinic hydrocarbons, and wherein uncondensed compreseed light hydrocarbons are further fractionated to recover a recycle stream containing at least 90 mole percent ethene.

17. The process of claim 12 wherein isobutane is reacted with propene and/or butylene in the seconday stage in the presence of a liquid phase acid catalyst at a pressure of about 1500 to 3000 kPa.

18. A process for converting oxygenated organic feedstock to liquid hydrocarbons comprising the steps of contacting a lower aliphatic oxygenate feedstock with zeolite catalyst in a primary catalyst state at low pressure and elevated temperature to convert at least a portion of the oxygenate feedstock to hydrocarbons containing $C_2$-$C_4$ olefins and $C_5+$ hydrocarbons;

separating primary stage effluent to provide an aqueous liquid byproduct stream, a heavy hydrocarbon liquid stream rich in $C_5+$ hydrocarbons and a light hydrocarbon vapor stream rich in in $C_2$-$C_4$ olefins;

compressing at least a portion of the olefinic light hydrocarbon stream in a plurality of compression stages to condense a liquid olefinic hydrocarbon stream rich in propene and butylenes;

fractionating uncondensed compressed light hydrocarbons to recover a recycle stream containing at least 90 mole percent ethene;

further reacting the condensed liquid olefinic hydrocarbon stream with $C_4+$ isoparaffin in a secondary alkylation stage with liquid phase acid catalyst to convert at least a portion of $C_3$-$C_4$ olefins to a heavier $C_7+$ liquid hydrocarbon product stream comprising alkylate gasoline; and further contacting said ethene-rich gaseous stream under conversion conditions with zeolite catalyst in the primary catalyst stage, thereby increasing yield of $C_3+$ olefins.

19. The process of claim 18 wherein isobutane is reacted with propene and/or butylene in the secondary stage in the presence of a liquid phase HF acid catalyst at a pressure of about 1500 to 3000 kPa; and wherein primary stage conversion is conducted at a temperature of about 425° C. to 550° C. and pressure of about 100 to 800 kPa over ZSM-5 type catalyst.

* * * * *